United States Patent [19]

Riley

[11] 4,331,818
[45] May 25, 1982

[54] CHIRAL PHOSPINE LIGAND

[75] Inventor: Dennis P. Riley, Forest Park, Ohio

[73] Assignee: The Procter & Gamble Company, Cincinnati, Ohio

[21] Appl. No.: 132,475

[22] Filed: Mar. 19, 1980

[51] Int. Cl.³ .............................................. C07F 9/50
[52] U.S. Cl. .................................................... 568/17
[58] Field of Search ......................................... 568/17

[56] References Cited

U.S. PATENT DOCUMENTS 3,382,173 5/1968 Zorn et al. ......................... 568/17 X
3,798,241 3/1974 Kagan et al. ..................... 260/446 X
3,978,101 8/1976 Aviron-Violet .................... 568/17 X

OTHER PUBLICATIONS

King et al., "1,2-Bis(diphenylphosphino)-1-phenylethane: A Chiral Ditertiary Phosphine Derived from Mandelic Acid Used as a Ligand in Asymmetric Homogeneous Hydrogenation Catalysts", *J. Org. Chem.*, vol. 44, No. 10 (1979), pp. 1729–1731.
Brown et al., "R-Phenyl Bis Diphenylphosphinoethane; Structural Studies Pertaining to Rhodium-Catalyzed Asymmetric Hydrogenation," *Tetra Let.*, No. 50 (1979), pp. 4859–4862.
Lauer et al, J. Organomet-Chem 177 309–312 (1979)
Vineyard et al, JACS 99 5046 (1977).
Valentine et al, Synthesis, 329–356 (1978)
Kagan et al, JACS 94 6429 (1972).
Halpern et al, J.A.C.S. 99 8055 (1977).
Fryzuk et al., J.A.C.S. 100 7556 (1978), JACS 99 6262 (1977).
Kosolopoff et al, Organic Phosphorus Compounds, Wiley Intersc., N.Y., vol. 1, pp. 202–210 (1972).

*Primary Examiner*—Helen M. S. Sneed
*Attorney, Agent, or Firm*—Michael J. Roth; Eric W. Guttag; Richard C. Witte

[57] ABSTRACT

The chiral phosphine ligand (R)-1,2-bis(diphenyl-phosphino)-1-cyclohexylethane, when complexed to Rh(I), functions as a superior chiral hydrogenation catalyst. The chiral phosphine ligand is more stereochemically rigid than previous compounds; consequently, virtually optically pure materials can be produced from the chiral hydrogenation of prochiral compounds using the catalyst of this invention. This catalyst is especially useful in the chiral hydrogenation of alpha-acylamido acrylic acids.

3 Claims, No Drawings

CHIRAL PHOSPHINE LIGAND

TECHNICAL FIELD

The present invention relates to novel metal-phosphine chiral hydrogenation catalysts. A number of commercially valuable materials having asymmetric centers can be prepared by hydrogenation of appropriate olefinic or ketonic starting materials. However, the chemical, biologic, or medical utility of many such materials is stereochemically dependent. That is, one stereoisomer is preferred to the other, or either isomer is preferred to the racemic mixture. Thus, workers in the art are constantly searching for hydrogenation catalysts which favor the formation of specific stereoisomers from prochiral substrates.

In the past, several rhodium (I) complexes containing chiral phosphine ligands have been reported to function as chiral hydrogenation catalysts. In general, it has been observed that those phosphines which are more stereochemically rigid produce higher optical yields (i.e., a greater proportion of the desired optical isomer).

It has recently been shown that a five membered chelate-ring-forming phosphine containing the chirality on a ring backbone carbon can function as a chiral hydrogenation catalyst. The rationale is that the chelate ring is constrained to one conformation, thus giving a "rigid" phosphine and consequently a fixed phenyl group orientation. The fixed phenyl groups then provide a source of discrimination between the groups on the coordinated olefin and the catalyst. This stereochemical effect is the suspected source of the high selectivities observed for these catalysts.

However, to obtain a high optical yield, both a large preference for one of the diastereomeric complexes and, if the substrate is an unsaturated molecule, a large preference for an interaction between the chiral center and one of the enantio- or diastereo faces of the substrate in the activated complex must exist. That is, a low optical yield obtained with a chiral hydrogenation catalyst must be due either to a low stereo-specificity in the catalyst-substrate interaction, and/or to a low free energy difference between the diastereomeric catalyst-substrate complexes at the equilibrium. As a consequence, a rational improvement of the optical yield in asymmetric catalysis is still very difficult and the main successes have been reached in a purely empirical way.

The present invention is the result of efforts to produce a more stereochemically rigid chiral bidentate phosphine ligand.

BACKGROUND ART

During the last several years a large number of rhodium (I) complexes containing chiral phosphine ligands have been reported to function effectively as chiral hydrogenation catalysts. See, for example, D. Valentine and J. W. Scott Synthesis, 329 (1978); M. Lauer, O. Samuel, and H. B. Kagan, J. Orgmet. Chem., 177, 309-12 (1979); and P. Pino and G. Consiglio in, Fundamental Research in Homogeneous Catalysis III, ed. M. Tsutsui, Plenum, New York, 1979, p. 519.

A number of references also describe the chemical and stereochemical mechanisms of these asymmetric homogeneous hydrogenation catalysts. See J. Halpern, D. P. Riley, A. S. C. Chan, J. J. Pluth, J. Amer. Chem. Soc., 99, 8055 (1977); A. S. C. Chan., J. J. Pluth, and J. Halpern, Inorg. Chim. Acta, 37, L477 (1979); D. A. Slack, I. Greveling, and M. C. Baird, Inorg. Chem., 18 (11), 3125 (1979); J. M. Brown and B. A. Murrer, Tett. Lett., 50, 4859 (1979); J. M. Brown, P. A. Chaloner, and P. N. Nicholson, J.C.S. Chem. Commun., 646 (1978); J. Halpern A. S. C. Chan, D. P. Riley, and J. J. Pluth, Adv. Chem. Ser., 173, ed. R. B. King, ASC, Wash. D.C., 1979, p. 16-25. W. S. Knowles, B. D. Vineyard, M. J. Sabacky, and B. R. Stults, in Fundamental Research in Homogeneous Catalysis III, ed. M. Tsutsui, Plenum, New York, 1979, p. 537; and C. Detellier, G. Gelbard, and H. M. Kagan, J. Amer. Chem. Soc., 100, 7556 (1978).

M. D. Fryzuk and B. Bosnich, JACS, 100, 5491 (1978) and JACS, 99, 6262 (1977) describe the preparation of certain rhodium-phosphine chiral catalysts.

DISCLOSURE OF THE INVENTION

The present invention provides phosphine compounds of the formula

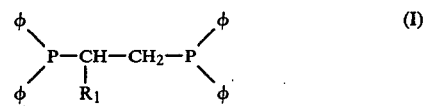

wherein $R_1$ is cyclohexyl or substituted cyclohexyl.

Catalysts prepared incorporating the phosphine compounds of formula (I) are outstanding chiral hydrogenation catalysts, providing extremely high optical yields in the reduction of prochiral substrates. Such chiral catalysts are prepared, generally, by the formation of coordination complexes with transition metal systems, in which the phosphine compound forms a bidentate ligand to the transition metal atom in the complex. Thus, the present invention provides compounds ("complexes") of the formula

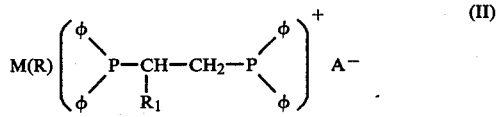

wherein M is a transition metal, R is a chelating diene, $R_1$ is as defined in formula (I), and $A^-$ is a non-coordinating anion.

The catalyst of this invention, in comparison to art-disclosed catalysts providing similar optical yields, offers the advantage of being easily prepared from naturally occurring, readily available forms of mandelic acid. In addition, since chiral catalysts owe their stereo-specificity to the chiral nature of the phosphine ligand, the catalyst of the present invention offers the advantage of being prepared from an optically active starting material, so that the desired chirality of the catalyst can be "built in" at the time the phosphine ligand is made, by selecting the appropriate, optically pure mandelic acid starting material. (S)(+) mandelic acid yields a catalyst in the (R)- configuration, which provides (S)- or L- products. Conversely, (R)(+) mandelic acid is converted to the (S)-catalyst, which yields D- or (R)-products. This feature obviates the need for laborious separation of a racemic mixture of phosphines into the respective isomeric forms before the catalyst can be used.

The present invention also provides a method for the chiral reduction of a prochiral olefin or ketone substrate, by reacting the substrate with hydrogen in the presence of a catalytic amount of a compound of formula (II).

Olefin substrates which are especially susceptible to chiral hydrogenation by the catalysts of this invention, and which can be hydrogenated to products which are very commercially desirable in optically pure form, are the alphaacylamido acrylic acids and their salts, esters, and amides. Such compounds have the formula

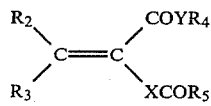

wherein $R_2$ and $R_3$ are H-, substituted or unsubstituted alkyl, cycloalkyl or aryl, $R_4$ is H or alkyl, X and Y are O or NH, and $R_5$ is substituted or unsubstituted alkyl or aryl.

The resulting products (after hydrolysis) are the corresponding amino acids, in virtually optically pure form, such as L-alanine, L-leucine, D-tryptophan, L-tyrosin, D-valine, and L-phenylalanine, the desired optical isomer being obtained in each case by selection of the appropriate catalyst isomer. Similarly, by derivatization of the amido acrylic acid starting material, the corresponding amino acid derivatives can be prepared, in very high optical yield. For example, alphaacetamido-3,4-dihydroxy cinnamic acid can readily be hydrogenated to N-acetyl-3,4-dihydroxy-L-phenylalanine which, by hydrolysis, can be converted to 3,4-dihydroxy-L-phenylalanine (levodopa), well known for its usefulness in treating the symptoms of Parkinson's disease. In similar manner, other L-phenylalanine derivatives can be prepared which are useful intermediates in the preparation of L-aspartyl-L-phenylalanine-based synthetic sweeteners.

Other prochiral olefins suitable for reduction by the catalysts of this invention are exemplified by atropic acid (α-phenyl propenoic acid), which can be reduced to α-phenyl propionic acid, useful in pharmaceutical syntheses.

Ketone substrates include acetophenone, which is reduced to styralyl alcohol, useful in the perfumery and flavoring arts.

The symbol "$\phi$", when used herein, represents a phenyl group.

The term "Cycphos", when used herein, refers to the phosphine of formula (I) wherein $R_1$ is cyclohexyl. The expression "xs", when used herein, indicates that the reagent or catalyst is used in stoichiometric excess. By "transition metal" herein is meant those elements which are capable of using penultimate shell orbitals as well as outermost shell orbitals in bonding. In particular, the transition metals include elements 21 through 29 (scandium through copper), 39 through 47 (yttrium through silver), and 57 through 79 (lanthanum through gold) and all known elements from 89 (actinium) on.

By "chelating diene" herein is meant an alkene or cycloalkene having at least two C=C bonds, capable of forming a bidentate ligand in a coordination complex with the transition metal. Such dienes include norbornadiene, and the 1,5-dienes, especially 1,5-cyclooctadiene.

By "non-coordinating anion" herein is meant an anionic moiety which does not, in the particular reaction mix employed, coordinate with the transition metal-phosphine-diene system to form an insoluble complex.

By "prochiral substrate" herein is meant a compound containing an olefinic or ketonic (double) bond which can be reduced to form an asymmetric carbon center in the compound.

All percentages herein are by weight, unless otherwise indicated.

Synthesis

The chiral phosphine ligand component of the catalyst of this invention can be synthesized as shown in the following scheme in over 30% overall yield.

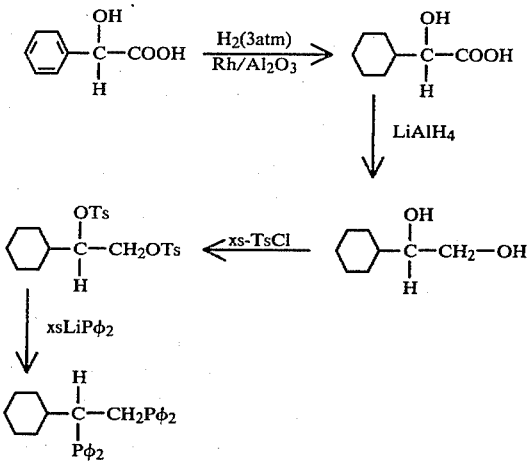

The synthesis is conducted using some of the techniques of Fryzuk and Bosnich (see Background Art Section). The key step in this sequence is the displacement of the tosylates with diphenylphosphide. In order to maximize this step—discourage elimination—the reaction is best carried out at −10° C. with a slight excess of LiP$\phi_2$. Other salts of the diphenylphosphide can be used, NaP$\phi_2$ and KP$\phi_2$, but the yields are diminished and the product phosphines have lower optical rotations. Apparently, there are some association effects. This is in contrast to the reported synthesis of the phenyl analog, which was conducted in high yield from mandelic acid using NaP$\phi_2$.

The transition metal complex is formed, in general, by simply mixing the Cycphos ligand with the transition metal-diene in an appropriate solvent.

Hydrogenation and Catalyst Removal

Using the cationic rhodium phosphine complex [Rh(R)-(1,2-bis(diphenylphosphino)-1-cyclohexylethane) (norbornadiene)]PF$_6$ as a convenient catalyst, the asymmetric hydrogenation of a number of olefinic and ketonic substrates has been studied.

These reductions were carried out in a number of solvents, including methanol (MeOH), tetrahydrofuran (THF), ethyl acetate (EtOAc), and methylene chloride (CH$_2$Cl$_2$). In all cases, the rates and optical yields were only slightly sensitive to solvent effects. This is in contrast to other, art-disclosed rhodium-phosphine catalysts, which in many cases are strongly solvent-dependent.

The reduction of alpha amide acrylic acid substrates was generally very fast at 25° C. and 1 atmosphere H$_2$. Turnover numbers range from as high as several hundred h$^{-1}$ for the least sterically encumbered olefin, alpha acetamidoacrylic acid, to ca. 2 h$^{-1}$ for the most sterically encumbered olefin, alpha acetamidoindolylacrylic acid. These rates are comparable to those reported in the literature for other rhodium-phosphine catalysts. Less activated substrates require higher temperatures and pressures to attain reasonable reaction rates.

Typically, catalyst:substrate ratios of 1:125 were employed for convenience. But catalyst to substrate ratios as low as 1:1000 can be successfully employed with no effect on the optical yield. Since the catalyst solutions are somewhat air sensitive, oxygen must be rigorously excluded at these latter, low catalyst levels.

The term "catalytic amount", when used herein, means any amount of catalyst which fosters the hydrogenation of the substrate, preferably 1:1000 catalyst:substrate or greater. All catalyst:substrate ratios herein are on a molar basis.

It is to be understood that the compounds referred to herein as "catalyst" are, in actual operation, catalyst precursors, which are converted to the active catalyst species in situ, through interaction with hydrogen in the reaction mix.

BEST MODE

EXAMPLE I

Preparation of (R)-1,2-Bis(diphenylphosphino)cyclohexylethane-"(R)-Cycphos"

A. (S)(+)-Hexahydromandelic Acid (S)(+)-Mandelic acid (76.0 g) was dissolved in 440 ml methanol containing 5 ml glacial acetic acid. The phenyl ring was entirely reduced in the presence of 5 gm. of 5% rhodium-on-alumina catalyst under 100 psi $H_2$ pressure in 10 hrs. Following filtration of the solution through Celite ® (diatomaceous earth) to remove the catalyst, the methanol was removed via a rotary evaporator. The resulting white solid was dissolved in 1 liter (l) of hot diethyl ether and filtered while hot. The volume of the solution was reduced to 400 ml and 250 ml cyclohexane was added. The ether was then removed and the resultant cyclohexane solution was stored several hours under refrigeration. White crystals of the desired product formed and were collected via filtration. The solid was dried overnight in vacuo at 40° C. Seventy-one grams of (S)(+)-hexahydromandelic acid were obtained for a 90% yield: m.p. 128°–129° C. (lit., 129° C.) and $[\alpha]_D^{23} = +23.5°$ (1, HOAc) (lit. $[\alpha]_D^{23} = +25.5$ (1.1, HOAc) for the (R) (+) isomer.

B. (S)-Cyclohexyl-1,2-ethanediol (S)(+)-Hexahydromandelic acid (195 g, 1.23 mol) in 1 liter dry THF was added dropwise over a period of 2 hrs to a stirred suspension of a stoichiometric excess of lithium aluminum hydride (LiAlH$_4$) (107 g, 2.82 mol) in 2 l of dry THF at 0° C. After the addition was complete, the solution was warmed to 25° C. and refluxed for 2 hrs. The reaction was then cooled to room temperature and the excess LiAlH$_4$ carefully quenched by dropwise addition of 175 ml H$_2$O, followed by 21.5 ml 4 N NaOH, and finally with 400 ml H$_2$O. The mixture was then refluxed for 1 hr and filtered. The alumina cake was washed 5 times with 800 ml portions of boiling THF. The filtrates were combined and reduced to dryness to yield a yellowish oil. This oil was dissolved in 1.5 l of hot diethyl ether. To this solution was added MgSO$_4$ and activated charcoal. The solution was filtered and the filtrate reduced to dryness to give a colorless oil which on standing crystallized to give the desired diol. Yield was 176 g (1.22 mol): 99% yield. Infrared spectra showed complete reduction. This material was then used directly to prepare the ditosylated alcohol.

C. (S)-Cyclohexyl-1,2-ethanediol-di-p-toluenesulfonate

The diol from step B (176 g, 1.22 mol) was dissolved in 125 ml dry pyridine and this solution was then added dropwise over ½ hr to an ice-cold solution containing 530 g (2.8 mol) of p-toluenesulfonyl chloride (TsCl) in dry pyridine. The solution was stirred at 0° C. for 6 hrs, by which time white needles of pyridine hyrochloride had formed. The reaction was then stirred at 25° C. for an additional 18 hrs. At this point several small portions of ice were added with vigorous shaking to destroy excess TsCl. The product was then poured onto 2.5 l of ice; 520 ml conc HCl (12 N) was added and the mixture was stirred vigorously for 1 hr. The solid was collected by filtration and washed with copious amounts of water. The solid was redissolved in 1.6 l of CH$_2$Cl$_2$ and washed 2× with 400 ml of 5 N HCl and then washed once with 600 ml H$_2$O. The organic layer was dried over MgSO$_4$ and activated charcoal was added. The solution was filtered through Celite ® and the volume reduced by ½ and then while hot (~40° C.), cyclohexane was added to the cloudpoint (~1 liter). The solution was allowed to cool slowly; a solid mass of white crystals formed. After storing at 0° C. for several hrs, the product was collected by filtration to yield 445 g of the desired ditosylate. Yield was 80%. The product $^1$H NMR was consistent with the desired structure and a satisfactory elemental analysis was obtained: Anal. Cal'd. for $C_{22}H_{28}O_6S_2$: C, 58.38%; H, 6.24%; S, 14.17%. Found: C, 58.90; H, 6.41%, and S, 14.0. The material was also optically active $[\alpha]_{23}^D = -3.7°$ (1.5, CHCl$_3$).

D. (R)-1,2-bis(diphenylphosphino)cyclohexylethane

A solution containing 45.3 g (0.1 mol) of the ditosylate of step C, dissolved in 200 ml of dry degassed THF, was added dropwise under N$_2$ over 1 hr to an ice-cold stirred solution containing 0.325 mole lithium diphenylphosphide. After the addition was complete, the solution was stirred for an additional hour at 25° C. Degassed H$_2$O (250 ml) was then added and the THF was distilled off under vacuum. This produced a white oily residue which was frozen (to inhibit atmospheric oxidation of the phosphine) and extracted while cold under N$_2$ with three 200 ml portions of cold diethyl ether. The ether was then added directly with vigorous stirring to a degassed solution of 21.7 g Ni(ClO$_4$)$_2$.6H$_2$O in 50 ml absolute ethanol. A deep red-colored solution formed to which was added slowly a hot saturated ethanolic solution containing 21.7 g of sodium thiocyanate. The solution turned deep reddish-brown and was stirred for two hours. The ether was then removed by rotary evaporator and the remaining ethanol solution was heated to boiling to dissolve all the solids. While the solution was kept warm, diethyl ether was added (~2-3 l) to precipitate the red-brown bis(R-Cycphos) Ni-thiocyanate complex. The solid was collected by filtration and dried in vacuo to yield 21.7 g of nickel complex (34%).

The nickel complex (21.7 g) was slurried under N$_2$ in 100 ml of refluxing 95% ethanol. To this hot solution was added at a brisk dropwise rate 6.1 g NaCN in 75 ml H$_2$O. The solution was refluxed for an additional hour, after which a yellow-orange solution formed, along with globules of an oil. Upon cooling the oil hardened on the bottom of the vessel and after further cooling at 0° C. for an hour (until water layer began to freeze), the aqueous layer was decanted. The oily solid was dissolved under N$_2$ in 150 cc hot abs. EtOH and then filtered. Upon cooling, a white solid mass formed and was collected by filtration and dried in vacuo. The yield of crude product was 17.7 g (32% from the ditosylate). This was recrystallized under $N_2$ from a minimal volume of hot abs EtOH (~110 ml) to yield 11.7 g of white needles. A second crop of the same optical rotation were later collected to afford a total yield of 13.7 g (25% yield from the ditosylate). $[\alpha]_{25}^D = +103.3°$ (1, THF under $N_2$). Subsequent recrystallizations did not change the rotation. Anal. calcd. for $C_{32}H_{34}P_2$: C, 79.97; H, 7.13; P, 12.89. Found: C, 80.07; H, 7.06; P, 13.01.

EXAMPLE II

[Rh((R)-Cycphos)(NBD)]PF$_6$ 2.0 g of rhodium norbornadiene (NBD) chloride dimer [(Rh(NBD)Cl)$_2$] were dissolved in acetone under $N_2$ and 2.2 g AgPF$_6$ added. The AgCl was removed by filtration and the Cycphos ligand (4.5 g) was added slowly. The volume of the acetone solution was then reduced to 15 ml and filtered through Celite ®. Then while hot, methanol was added (~50 ml), and upon removing more solvent in vacuo and cooling an orange precipitate formed. Two crops of the orange product were obtained, combined, washed with diethyl ether and dried in vacuo. Total yield was 5.4 g (74% yield based on starting phosphine). Anal. calcd. for $C_{39}H_{42}P_3F_6Rh$: C, 57.09; H, 5.16; P, 11.32. Found: C, 56.63; H, 5.40; P, 11.01. Electronic spectrum in methanol: $\lambda^{MAX}=474$ nm ($\epsilon=900$).

INDUSTRIAL APPLICABILITY

While the present invention provides an especially preferred chiral catalyst of the formula

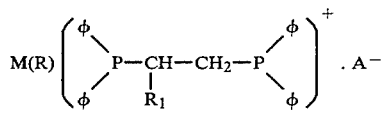

wherein M is rhodium, R is norbornadiene, R$_1$ is cyclohexyl, and A$^-$ is PF$_6^-$, this formula admits of certain variations.

In particular, any chelating diene can be substituted for the norbornadiene used above. Where chelating dienes other than norbornadiene are used, the 1,5 dienes, and especially 1,5-cyclooctadiene, will be found to be useful.

Similarly, any non-coordinating anion can be substitute for the PF$_6^-$, such as BF$_4^-$, or ClO$_4^-$. Since the present invention advantageously provides homogeneous hydrogenation catalysts, i.e., catalysts which are soluble in the hydrogenation reaction mix, the anion should be selected to provide a complex which does not crystallize out of the substrate-solvent mixture. At the same time, the ClO$_4^-$ form can be used under appropriate conditions to produce crystals of sufficient size for x-ray crystallographic studies of the catalyst's structure.

The following examples are illustrative of the broad industrial utility of the present invention, without intending to be limiting thereof. Numerous other variations, especially in the area of hydrogenation substrates, while not specifically enumerated herein, are equally contemplated and fully encompassed by this invention.

EXAMPLES III-XIII

Asymmetric hydrogenations were conducted as described hereinabove. In particular, all solvents used for the hydrogenations were dried and degassed prior to use. In all cases the procedure involved loading the accurately weighed substrate (1-2 g) and catalyst precursor, [Rh((R)-Cycphos)(NBD)]PF$_6$, into a dimpled flask which was transferred to an inert atmosphere glove box. To the flask was added the desired amount of solvent (generally 20 ml). The flask (sealed via a stopcock) was then transferred to the hydrogenation line. After several pump-down/purge cycles, the hydrogenations were begun via vigorous shaking. Reactions were allowed to go to completion; progress of the reaction was followed by monitoring the H$_2$ uptake.

The workup of acid products is carried out by removing all the solvent on a rotary evaporator and then dissolving the residue in CH$_2$Cl$_2$ or other suitable (non-water miscible) solvent. The organic layer is then extracted once with 1 N NaOH solution. The organic phase then contains the catalyst residues and can be discarded. The aqueous layer is filtered to remove any suspended material and then acidified with conc. HCl. The water layer is extracted with Et$_2$O or other suitable organic solvent and this organic layer is then dried over Na$_2$SO$_4$. Filtration followed by removal of all solvent affords solid (generally crystalline) products which are then weighed directly to obtain optical rotations and also $^1$H NMR spectra. For some of the acids (N-acetylalanine and N-acetyltyrosine) which are H$_2$O soluble, the neutralization step is followed by removal of all H$_2$O. The solid residue is then extracted with an organic solvent to dissolve the product and leave the NaCl behind.

When esters are produced, the catalyst removal is effected by silica gel chromatography using 30% EtOAc in hexane as the eluent; for the alcohol products either silica gel chromatography or vacuum distillation effectively separates the catalyst residue from the product. Optical yields (%) were obtained as follows.

| Example | Substrate | Final Product | Solvent | | | |
|---------|-----------|---------------|---------|------|------|---------|
|         |           |               | THF | MeOH | EtOAc | CH$_2$Cl$_2$ |
| III | 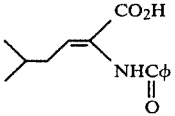 CO$_2$H, NHCφ(=O) | L-2-Amino-5-methyl hexanoic acid | | 94 | 95 | 91 |
| IV | 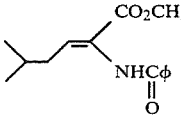 CO$_2$CH$_3$, NHCφ(=O) | L-2-Amino-5-methyl hexanoic acid | | 86 | 84 | 90 |

-continued

| Example | Substrate | Final Product | Solvent | | | |
|---|---|---|---|---|---|---|
| | | | THF | MeOH | EtOAc | CH$_2$Cl$_2$ |
| V | (CH$_3$)$_2$CH-C(=CHR)-CO$_2$H, NHC$\phi$(=O) | L-leucine | 89 | 90 | 94 | |
| VI | $\phi$CH=C(CO$_2$H)(NHC$\phi$(=O)) | L-phenylalanine | 94 | 93 | 93 | |
| VII | $\phi$CH=C(CO$_2$Et)(NHC$\phi$(=O)) | L-phenylalanine | | 88 | 87 | |
| VIII | $\phi$CH=C(CO$_2$H)(NHCCH$_3$(=O)) | L-phenylalanine | 83 | 84 | 91 | |
| IX | HO-C$_6$H$_4$-CH=C(CO$_2$H)(NHC$\phi$(=O)) | L-tyrosine | 98 | | 92 | |
| X | indol-3-yl-CH=C(CO$_2$H)(NHCCH$_3$(=O)) | L-tryptophan | 81 | 83 | | |
| XI | CH$_2$=C(CO$_2$H)(NHCCH$_3$(=O)) | L-alanine | 87 | | 96 | |
| XII | CH$_2$=C(CO$_2$H)($\phi$) | Hydratropic acid | | 8* | | |
| XIII | $\phi$-C(=CH$_2$)-O-C(=O)CH$_3$ | Styralyl alcohol | | 6** * | | |

*100 Atm. H$_2$; triethylamine added to solvent
**Hydrogenation 72% complete

EXAMPLES XIV–XVI

In order to compare the catalyst of the present invention with those of the art, the following hydrogenations were conducted, using rhodium complexes of 4 chiral phosphine ligands described in the literature and Rh(NBD)(R)-Cycphos PF$_6$.

Catalysts (phosphine ligands)

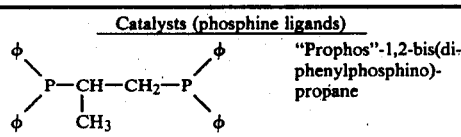

"Prophos"-1,2-bis(diphenylphosphino)-propane

-continued

Catalysts (phosphine ligands)

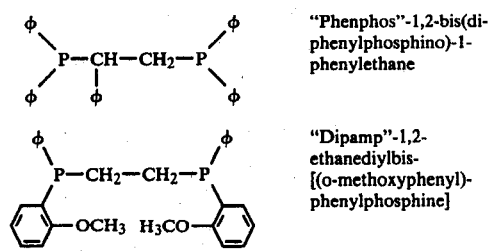

"Phenphos"-1,2-bis(diphenylphosphino)-1-phenylethane

"Dipamp"-1,2-ethanediylbis-[(o-methoxyphenyl)-phenylphosphine]

Catalysts (phosphine ligands)

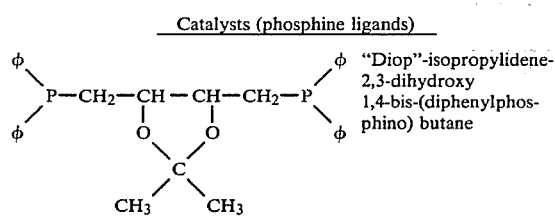

"Diop"-isopropylidene-2,3-dihydroxy 1,4-bis-(diphenylphosphino) butane

Reaction

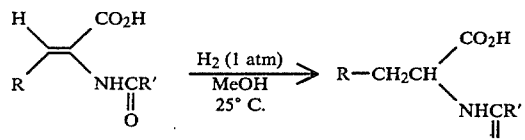

| Example | Substrate | Catalyst | % Optical Yield | L/D Ratio |
|---|---|---|---|---|
| XIV | R = CH₂—CH(CH₃)CH₃ | (R)-cycphos | 94 | 32 |
|  | R' = φ | (R)-prophos | 85 | 12 |
| XV | R = R' = φ | (R)-cycphos | 94 | 32 |
|  |  | (R)-prophos | 90 | 19 |
|  |  | (S)-phenphos | 84 | 11* |
|  |  | (R)-dipamp | 93 | 27 |
|  |  | (+)-diop | 64 | 5* |
| XVI | R = —CH(CH₃)CH₃ | (R)-cycphos | 92 | 24 |
|  |  | (R)-prophos | 83 | 11 |

R' = φ

*D/L ratio

EXAMPLES XVII–XIX

In order to show the relative solvent independence of the catalyst of this invention, it was compared with the prophos catalyst of Examples XVII–XIX in the following hydrogenation, using 1 atm. $H_2$ and a 1:125 catalyst:substrate ratio.

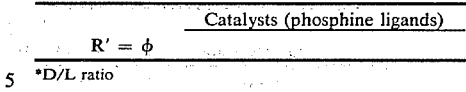

| Example | Catalyst | Solvent | % Optical Yield | L/D Ratio |
|---|---|---|---|---|
| XVII | R-Cycphos | MeOH | 95 | 39 |
|  | R-Prophos | MeOH | 85 | 12 |
| XVIII | R-Cycphos | CH₂Cl₂ | 91 | 21 |
|  | R-Prophos | CH₂Cl₂ | 91 | 21 |
| XIX | R-Cycphos | EtOAc | 94 | 32 |
|  | R-Prophos | EtOAc | 89 | 17 |

In addition, reaction rates observed with the catalyst of this invention were approximately equal to those observed with the art-disclosed prophos catalyst.

What is claimed is:

1. A compound of the formula

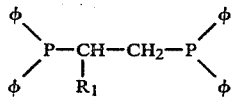

wherein $R_1$ is cyclohexyl.

2. A compound according to claim 1 which is (R)-1,2-bis-(diphenylphosphino)-1-cyclohexylethane.

3. A compound according to claim 1 which is (S)-1,2-bis-(diphenylphosphino)-1-cyclohexylethane.

* * * * *